United States Patent

Ovsyanko

(10) Patent No.: US 9,103,824 B2
(45) Date of Patent: Aug. 11, 2015

(54) BIOSENSOR SYSTEM FOR ACTUATING MAGNETIC PARTICLES

(75) Inventor: Mykhaylo M. Ovsyanko, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 515 days.

(21) Appl. No.: 13/129,818

(22) PCT Filed: Jul. 22, 2009

(86) PCT No.: PCT/IB2009/053168
§ 371 (c)(1),
(2), (4) Date: May 18, 2011

(87) PCT Pub. No.: WO2010/058303
PCT Pub. Date: May 27, 2010

(65) Prior Publication Data
US 2011/0221427 A1    Sep. 15, 2011

(30) Foreign Application Priority Data

Nov. 19, 2008  (EP) .................... 08169405

(51) Int. Cl.
*G01N 33/543*   (2006.01)
*G01N 27/74*    (2006.01)
(Continued)

(52) U.S. Cl.
CPC ........ *G01N 33/54333* (2013.01); *G01N 27/745* (2013.01); *G01N 33/54373* (2013.01); *G01N 21/552* (2013.01); *G01N 35/0098* (2013.01)

(58) Field of Classification Search
CPC . G01N 35/0098; G01N 27/745; G01N 11/14; G01N 33/54326; G01N 33/54333; G01N 33/54386; G01N 33/569; B01L 2400/043; B01L 2200/027; B01L 2200/0647; B01L 2200/0668; B01L 2300/069; B01L 2300/0816
USPC ......................................... 436/526
See application file for complete search history.

(56) References Cited

U.S. PATENT DOCUMENTS 5,053,344 A    10/1991   Zborowski
5,394,739 A *  3/1995    Garvey et al. ................ 73/54.23
(Continued)

FOREIGN PATENT DOCUMENTS

JP    01272973 A    10/1989
JP    05312786 A    11/1993
(Continued)

OTHER PUBLICATIONS

Luxton, Richard et al "Use of External Magnetic Fields to Reduce Reaction Times inan Immunoassay using Micrometer-Sized Paramagnetic Particles as Labels (Magnetoimmunoassay" Anal. Chem. 2004, vol. 76, pp. 1715-1719.

*Primary Examiner* — Bao Thuy L Nguyen
*Assistant Examiner* — Kyung Sung

(57) ABSTRACT

The application discloses a biosensor system (1) comprising: a biosensor cartridge (30), a first biosensor magnet assembly (10) for generating a magnetic field in the biosensor cartridge comprising two magnetic subunits (20a, 20b) each having a core (22a, 22b) with a top surface (24) separated by a gap (25), and wherein the sensor surface comprised by the biosensor cartridge is arranged above the top surfaces of the cores, wherein the two subunits are adapted to generate a magnetic field between the first subunit and the second subunit with magnetic field lines essentially in parallel to the sensor surface to exert forces at magnetic particles in the cartridge. By employing the system for controlling the movement of magnetic particles in immunoassays, more reliable test results are achieved.

18 Claims, 6 Drawing Sheets

(51) Int. Cl.
*G01N 21/552* (2014.01)
*G01N 35/00* (2006.01)

(56) References Cited

U.S. PATENT DOCUMENTS

| | | |
|---|---|---|
| 5,466,574 A | 11/1995 | Liberti |
| 5,779,907 A | 7/1998 | Yu |
| 6,018,241 A * | 1/2000 | White et al. ............... 324/207.2 |
| 6,136,182 A | 10/2000 | Dolan |
| 7,081,192 B1 | 7/2006 | Wang |
| 2006/0205093 A1 * | 9/2006 | Prins ........................ 436/526 |

FOREIGN PATENT DOCUMENTS

| | | |
|---|---|---|
| JP | 2000227419 A | 8/2000 |
| JP | 2002531811 A | 9/2002 |
| WO | 0032293 A1 | 6/2000 |
| WO | 2004078316 A1 | 9/2004 |
| WO | 2008107827 A1 | 9/2008 |
| WO | 2009095818 A1 | 8/2009 |

\* cited by examiner

BIOSENSOR SYSTEM FOR ACTUATING MAGNETIC PARTICLES

FIELD OF THE INVENTION

The invention relates to biosensor systems comprising a biosensor cartridge and a first biosensor magnet assembly with two magnetic subunits for use with the biosensor cartridge, and to a method for actuating magnetic particles in the biosensor cartridge.

BACKGROUND OF THE INVENTION

Various analytical procedures to detect an analyte in a test sample are known in the prior art.

For example, immunoassays use the mechanisms of the immune system, wherein antibodies and the respective antigens are capable of binding to each other.

This specific reaction mechanism is used to determine the presence or quantity of the antigen in a test sample. In particular, the antibody or the antigen (analyte of interest) is labeled to quantify the interactions between antibody and antigen. Common labels are, for example, fluorescent and chemiluminescent molecules, colored particles (beads) or radioisotopes.

Recently, magnetic labels have been used in microfluidic assays to detect the presence or quantity of an analyte. The use of magnetic labels as, for example, magnetic particles, also denominated as magnetic beads or beads, has several advantages. The magnetic particles can be actuated by applying a magnetic field such that the analytical procedure can be accelerated. Further, there is no magnetic background signal in the biological test sample influencing the detection of the magnetic particles.

However, these assays using magnetic labels require means for actuating the magnetic particles bound to the antigens to be immobilized near the sensor surface of the sensor cartridge, and for flushing away the remaining unbound magnetic particles not to influence the quantity measurement of the bound particles. Therefore, for example, two magnets may be arranged on opposite sides of the sensor cartridge, wherein the first magnet attracts the magnetic particles to move through the test sample toward the sensor surface, then the second magnet attracts unbound magnetic particles to move away from the sensor surface. In this configuration, the two magnets are mounted on a holding structure, and the holding structure mechanically moves the magnets toward or away from the sensor surface (see R. Luxton et al., "Use of External Magnetic Fields to reduce reaction times in an immunoassay . . . ", *Anal. Chem.* 2004, 76, 1715-1719).

Such a method is very laborious and time-consuming and needs a complex holding structure for arranging the two magnets on opposite sides of the sensor cartridge. Further, the first magnet arranged below the sensor cartridge controls the movements of the magnetic particles only in the direction perpendicular to the sensor surface, but not in the horizontal direction, the direction essentially parallel to the sensor surface. Therefore, areas with accumulations of unbound magnetic particles may exist in the cartridge next to areas with only few or maybe too less magnetic particles to bind with the antigens of interest. Further, unbound particles in peripheral regions in the cartridge may not easily and as fast as other particles be attracted by the second magnet so that these particles may remain in the cartridge. This may result in unreliable test results.

Generally, the particles of a test sample undergo several processes, e.g. particles approach to the sensor surface, bind to the sensor surface, unbind from the sensor surface, etc. In known biosensor systems, magnetic particles near by the magnet are usually actuated by the magnetic field and drawn towards the magnet. In this case, the quality and/or quantity of a signal received from the sensor surface next to the magnet will depend on time and thus not be reliable, since it would not only represent the bound particles, but also be influenced by unbound magnetic particles in remote sections in the cartridge which are actuated by the magnetic field and may thus move towards the sensor surface next to the magnet.

SUMMARY OF THE INVENTION

One object is to provide a biosensor system and method for controlling the movement of magnetic particles in the cartridge and thus for providing more reliable test results.

The invention discloses a bio sensor system with a biosensor cartridge, a first biosensor magnet assembly, in the following also referred to as first magnet assembly, for generating a magnetic field in the biosensor cartridge comprising two magnetic subunits each having a core with a top surface separated by a gap, and wherein a sensor surface comprised by the biosensor cartridge is arranged above the top surfaces of the cores, wherein the two subunits are adapted to generate a magnetic field between the first subunit and the second subunit with magnetic field lines essentially in parallel to the sensor surface to exert forces at magnetic particles in the cartridge. The term biosensor is herein used for all kinds of sensors appropriate for detecting biological substances or biological material. The term top surface is herein used for a part of the core on top of the core near to the sensor surface which has a different shape than the typical cylindrical shape of the core. The top surface is aligned in a direction to the sensor surface, whereas the core is usually aligned vertical. As the sensor surface is positioned between the cores this means the top surface encloses an angle with the core which is described in detail in the following. The top surfaces form the profile of the magnetic field. The biosensor system is compact, consumes little space, and permits a flexible control of movement of the magnetic particles. With the biosensor system described magnetic particles can be moved in several directions, especially in a direction to the left and right with regard to the Figs. The biosensor system enables to wash away excessive beads not bound to an assay from the sensor surface without breaking bindings of bound beads.

Particular examples of the invention are described in the dependent claims.

In an example of the biosensor system a second magnet assembly is arranged above the sensor surface for exerting a force on magnetic particles in the cartridge. The second magnet assembly can be designed similar to one of the two subunits. The second magnet assembly provides an additional magnetic field for exerting forces at the beads and is controllable together with the two subunits by the control means driving the two subunits and the top coil.

The first biosensor magnet assembly for generating a magnetic field is used in a biosensor system such that the spatial movement of magnetic particles in a biosensor cartridge may be controlled. By generating a magnetic field within the cartridge, analytes, typically antigens or substances, included in the test sample and labeled with magnetic particles and present in the vicinity of the first biosensor magnet assembly may be moved towards a sensor surface in the cartridge to bind to immobilized antibodies. The bound complex structure of antibody, antigen, which is the analyte to be tested, and magnetic particle functioning as a label may then be detected at the sensor surface such that the mere presence or even the quantity of the analyte in the test sample may be estimated or determined. A further inferior aspect is due to the changing of the magnetic field within the cartridge, magnetic particles present in the cartridge, but remote from the first biosensor magnet assembly may be hindered to move to the sensor surface. This further effect is shown in FIG. 1, where different areas of magnetic field lines are depicted. In areas denoted as B at the edge of the cartridge the magnetic particles or beads are hindered to pass because of the magnetic field lines and corresponding forces directed nearly perpendicular to the surface and building an obstacle for the beads. In other words magnetic walls are created between different areas at the cartridge.

According to FIG. 1, a biosensor system is provided, comprising a biosensor cartridge and a first biosensor magnet assembly for generating a magnetic field in the biosensor cartridge. At the biosensor cartridge the magnetic field lines are at one area B at the edge of the sensor surface of the cartridge directed in a way to block beads from passing the edge of the sensor surface.

A biosensor cartridge is a container or reservoir for receiving a fluid test sample containing the analyte, for example an antigen, of interest. Usually, the cartridge may have at least one plane base area, particularly a rectangular or circular or elliptical base area. The base area functions as a sensor surface at which the analyte of interest may be analyzed by detection procedures. Preferably, the cartridge or at least the plane base area of the cartridge is made, for example, from glass, cyclo-olefin (co)polmers, polyethylene, polystyrene, polycarbonate, or polymethylmetacrylate to enable an optical analysis of the test sample.

A biosensor cartridge may contain or may receive magnetic or magnetizable particles. "Magnetic" or "magnetizable" particles are influenced by application of a magnetic field and are magnetically responsive. For example, these particles are attracted or repulsed or have a detectable magnetic susceptibility or induction. In a preferred embodiment, these particles are paramagnetic or superparamagnetic particles and may be made from metals or metal oxides or composite materials such as ferrites, e.g. a magnetite. These particles may be beads or labels and are adapted to bind to a target moiety, e.g. an antibody and/or an antigen, the analyte of interest. Such a binding can occur directly or via a specific binding member as, for example, a protein captured by an antibody and/or a protein sandwiched between the particle and the antibody or antigen. In one embodiment of a biosensor cartridge, antibodies are immobilized via capture reagents at the sensor surface of the cartridge and provide a binding site for the antigen labeled with the magnetic or magnetizable particle.

In a particular embodiment at least one of the top surfaces may have an inclined section, different shapes are designable, as described later. In another example at least one of the top surfaces has a plane section on top of the top surface spaced between 0.1 mm to 5 mm from the sensor surface.

In a particular embodiment, at least one of the magnetic subunits may be an electromagnetic subunit.

The first magnet assembly of the biosensor system comprises at least two magnetic subunits. In particular, the magnetic subunits may be electromagnetic subunits comprising coils having a magnetizable (magnetically responsive) core inside each coil.

The core may be made of a ferromagnetic material. The first biosensor magnet assembly may be arranged in such a way that one of the poles of each subunit is adjacent to the sensor surface at one of the sides of the biosensor cartridge. In one embodiment, the subunits essentially have a cylindrical shape within the coil area and the two magnetic poles are present at the two ends of the cylinder (i.e. the base area and the top surface of the cylinder). The core of a subunit may have a diameter of between 0.01 and 5 mm, preferably between 0.02 and 2 mm, and the height of the core may be between 3 and 10 mm, preferably 5 mm.

In particular, the core of a magnetic subunit has a top surface, preferably arranged below the sensor surface of the cartridge, which may comprise a plane section and the inclined section. In a preferred embodiment, the plane section is arranged to be parallel to the sensor surface of the cartridge.

In a particular embodiment, the magnetic field strength of each subunit may be separately changeable by electrical control.

The term "separately changeable" means that the magnetic field of each subunit can be changed by electrical control independently from any change of the magnetic fields of the other subunit. If the subunits comprise electromagnetic coils as described above, the change of the magnetic field strength of a subunit may be carried out by changing the electric current flowing through the coil of a subunit. In this case, the "electrical control" is meant to be the control of the electric current flowing through the coils.

The bio sensor system of the present invention allows for a steering of the movement of magnetic or magnetizable particles, beads, for example labels, in the biosensor cartridge due to the changeable magnetic field of the first biosensor magnet assembly. Preferably, the particles can be steered to move directly to the sensor surface of the cartridge to save operation time. Further, an up-concentration of particles at a particular location on the sensor surface may be avoided by separately changing the magnetic field strength of the electromagnetic subunits: due to a separate control of each of the subunits, the magnetic field gradient, which is proportional to the force acting on the particles, may be regulated to move the particles in horizontal direction, i.e. essentially parallel to the sensor surface, and/or essentially vertical direction, i.e. perpendicular to the sensor surface.

In a particular embodiment, the whole analysis volume of the bio sensor cartridge, i.e. the volume that is analyzed in the biosensor assay, may be affectable by the magnetic field generated by the subunits.

The area of the sensor surface or the whole volume of the bio sensor cartridge may be affectable and/or penetrable by the magnetic field of the subunits. The volume of the cartridge is its inner volume (excluding any inlets or outlets for filling-in a test sample) into which a test sample including the analyte can be inserted. The area of the sensor surface of the cartridge is generally the plane base area of the cartridge onto which, for example, the magnetic or magnetizable particles and/or antibodies corresponding to the antigens as an example for an analyte to be determined can be immobilized. Advantageously, the biosensor cartridge is arranged adjacent to the first biosensor magnet assembly so that the whole volume of the cartridge is affectable and/or penetrable by the magnetic field of the subunits. In this case, all magnetic or magnetizable particles in the cartridge may be actuated and geometrical constraints within the cartridge may be avoided.

In a particular embodiment, the inclined section of a magnetic subunit may be inclined by 100° to 170°, preferably by 120° to 150°, more preferably by 130 to 140°, or by 135°, with reference to the perpendicular of the sensor surface of the biosensor cartridge.

In an embodiment, the inclined section is inclined towards the main axis of the core of a magnetic subunit. If the core essentially has the outer shape of a right circular cylinder, the main axis is the height axis of the cylinder.

In a particular embodiment, each of the top surfaces may have a plane section spaced between 0.1 mm to 10 mm from the sensor surface.

For example, the top surface of a core of a magnetic subunit may have the inclined section and may further comprise the plane section. In this case, the plane section may be arranged parallel to the sensor surface in the cartridge. The distance between the plane section and the sensor surface may be 0.1 to 10 mm, particularly 0.1 to 5 mm, more particular 0.1 to 3 mm. A close arrangement between core and sensor surface may provide for a high magnetic field density at the sensor surface and may thus provide for more reliable test results.

According to the invention, a method for actuating magnetic particles with a biosensor system according to the biosensor system is claimed. In arranging the biosensor cartridge adjacent to the first biosensor magnet assembly, the magnetic field generated by the first magnet assembly may affect a sensor surface in the cartridge to control the movement towards and away from the sensor surface in order to obtain reliable test results.

In a particular embodiment, the first biosensor magnet assembly and the biosensor cartridge used in the method of the invention are parts of the biosensor system as described above.

The method may allow to control the movement of magnetic or magnetizable particles in a biosensor cartridge to enable more reliable test results: An equal distribution of the particles in horizontal and/or vertical direction of the cartridge may be achieved and remaining unbound particles remote from the sensor surface may be hindered to move towards the sensor surface during the test procedure.

In a particular embodiment, the method may comprise a step of changing the polarity of at least one of the magnetic subunits.

For example, the system can have two different configurations, namely North-North configuration and North-South configuration, whereas South-South configuration and South-North configuration provide the same pattern of magnetic field lines as North-North configuration and North-South configuration, respectively. In changing the polarity of at least one of the subunits, the direction of the force due to the magnetic field and directed to a magnetic particle in the cartridge may be flipped. Preferably, the force directed onto a magnetic particle may be changed in sign due to the changing of the polarity of at least one of the magnetic subunits.

In a particular embodiment, the first biosensor magnet assembly may generate a pre-determined magnetic field gradient in a direction parallel and/or perpendicular to the sensor surface in the biosensor cartridge.

Preferably, the magnetic field gradient obtained in the biosensor cartridge is variable in a direction parallel and/or perpendicular to the sensor surface of the cartridge. In doing so, for example, the particles may be actuated by the gradient to arrange in pre-determined areas on the sensor surface in the biosensor cartridge to preferably calibrate the detection procedure.

In a particular embodiment, the inclined section may be inclined by 100° to 170°, preferably by 120° to 150°, more preferably by 130 to 140°, or by 135°, with reference to the perpendicular of the sensor surface of the biosensor cartridge.

In a particular embodiment, each of the top surfaces may have a plane section spaced between 0.1 mm to 10 mm from the sensor surface.

In particular, the subunits may be located on a base structure (particularly, with the subunits' base areas located on the base structure), preferably on a ferromagnetic yoke. In an embodiment, the base structure may be part of the subunits. A base structure may enable an easier handling of the first biosensor magnet assembly and may further avoid geometrical constraints which may arise if the subunits are not arranged in one plane. A ferromagnetic yoke as the base structure may strengthen the magnetic field of the first biosensor magnet assembly by concentrating the magnetic field lines of magnetic flux inside in the yoke and thus avoiding losses. In particular, the base structure may have the shape of a cuboid with a length and width of between 0.01 mm and 10 mm, preferably 5 mm or less than 5 mm, and a height (i.e. the direction toward the biosensor cartridge) of between 2 and 10 mm, preferably 4 mm.

In a particular embodiment, the biosensor system of the invention may further comprise control means adapted to separately switch or adjust the magnetic field strength of each subunit by electrical control. In particular, the control means may switch the orientation of magnetization in the magnetic subunits. The control means may be advantageous in order to obtain a pre-determined magnetic field gradient in the biosensor cartridge. The magnetic field strength can be increased or decreased separately for each subunit by the control means, for example by increasing or decreasing the electric current in the coils of the subunits. Hence, a pre-determined magnetic field gradient may be obtained in the bio sensor cartridge, and the obtained magnetic field gradient may easily be modified by the control means at any time of the analytical procedure. In particular, the control means may be adapted to vary the magnetic field gradient in a direction parallel (horizontal) and/or perpendicular (vertical) to the sensor surface of the biosensor cartridge. Due to the possibility of a separate adjustment of the magnetic field strength for each subunit, the magnetic flux density in the cartridge may be variable. Hence, magnetic or magnetizable particles in the biosensor cartridge may be controllable to move in a particular spatial direction, for example in horizontal direction, i.e. parallel to the sensor surface, or in vertical direction, i.e. perpendicular to the sensor surface. Thus, the diffusion of the particles in the cartridge may be controlled, e.g. accelerated or even slowed-down in each spatial direction, by using the control means for varying the magnetic field strength of the subunits.

In a particular embodiment, the biosensor system of the invention is a FTIR (Frustrated Total Internal Reflection) magnetic biosensor system. Due to the fact that optical beams and magnetic fields do generally not interfere with each other, optical detection methods for analyzing the presence and preferably the quantity of an analyte of interest in a test sample are advantageous if using magnetic or magnetizable particles as labels. Hence, external magnetic actuation may be well-suited for use with optical detection methods, since sensor disturbances by the magnetic field may be avoided.

These and other aspects of the invention will be apparent from and exemplified with reference to the embodiments described hereafter.

DETAILED DESCRIPTION OF EMBODIMENTS

Figure 1:
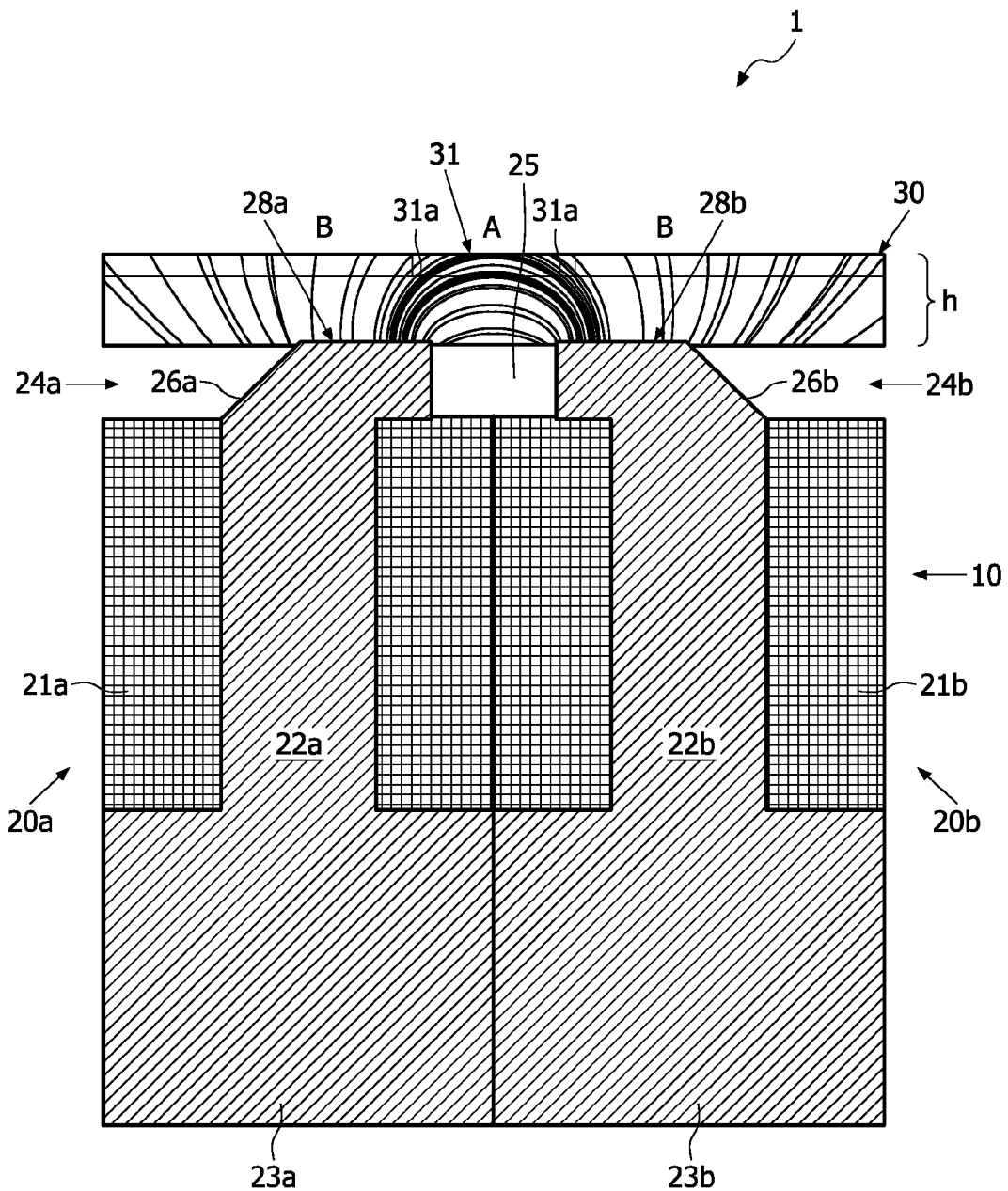
FIG. 1 schematically shows a cut of a side view of the set-up for a biosensor system according to one embodiment of the invention, with two magnetic subunits arranged below a cartridge having a sensor surface.

FIG. 1 shows an embodiment of a biosensor system 1 comprising a first biosensor magnet assembly 10 with two electromagnetic subunits 20a, 20b, which may be arranged on a base structure 23a, 23b, typically formed integrally with the subunits 20a, 20b. In one preferred embodiment, each subunit 20a, 20b comprises a coil 21a, 21b and a core 22a, 22b inside the coil 21a, 21b. By changing the electric current flowing through the coil 21a, 21b, the magnetic field strength of each subunit 20a, 20b may be electrically controlled. An example of a magnetic field strength is up to 40 kA/m, an example of a magnetic field gradient is up to $2*10^7$ A/m$^2$. Generally, the subunits 20a and 20b are arranged on one side of a biosensor cartridge 30 facing the magnetic subunits 20a and 20b. The biosensor cartridge 30 is shown in FIG. 1 as having a length dimension and a height h. In case a base structure 23a, 23b is used, the cartridge 30 is located adjacent to the subunits 20a and 20b such that the first magnet assembly 10 is located between the base structure 23a, 23b and the cartridge 30. In a particular embodiment, the base structure 23a, 23b may be a single yoke as discussed above. Further, the cartridge 30 may be arranged such that its volume is affectable and/or penetrable by the magnetic field of the first magnet assembly 10. In FIG. 1, the magnetic subunits 20a, 20b have North-South configuration such that the magnetic field lines provide the pattern in the cartridge 30 as shown in FIG. 1 and may penetrate a sensor surface 31 in the cartridge 30. The sensor surface 31 in the cartridge 30 serves for the detection of an analyte which is to be applied to the cartridge 30. The cores 22a, 22b of the subunits 20a, 20b comprise top surfaces 24a, 24b arranged on top of the cores, also denoted as tips in the following, which have inclined sections 26a, 26b and plane sections 28a, 28b on top, as depicted in FIG. 1. The plane sections 28a, 28b are preferably arranged closely to the cartridge 30, and/or parallel to the sensor surface 31 in the cartridge 30. After generation of a magnetic field in the cartridge 30 by the first biosensor magnet assembly 10, the magnetic field lines provide a pattern as shown in FIG. 1, wherein the field lines emanate perpendicularly from a top surface 24a, 24b of a core 22a, 22b. For the sake of clearness the magnetic field lines are drawn only in the area of the cartridge 30.

According to an embodiment of the method of the present invention, the sensor surface 31 of the cartridge 30 is arranged above the first magnet assembly 10 in FIG. 1, such that the magnetic field resulting from the magnetic subunits 20a, 20b penetrates the volume of the cartridge 30, in particular the whole analysis volume that is analyzed by the biosensor assay. Due to the inclined sections 26a, 26b of the top surfaces 24a, 24b of the subunits 20a, 20b, the movement of magnetic or magnetizable particles 2 present in the cartridge 30 or filled in the cartridge 30 may be particularly controlled.

Figure 2:
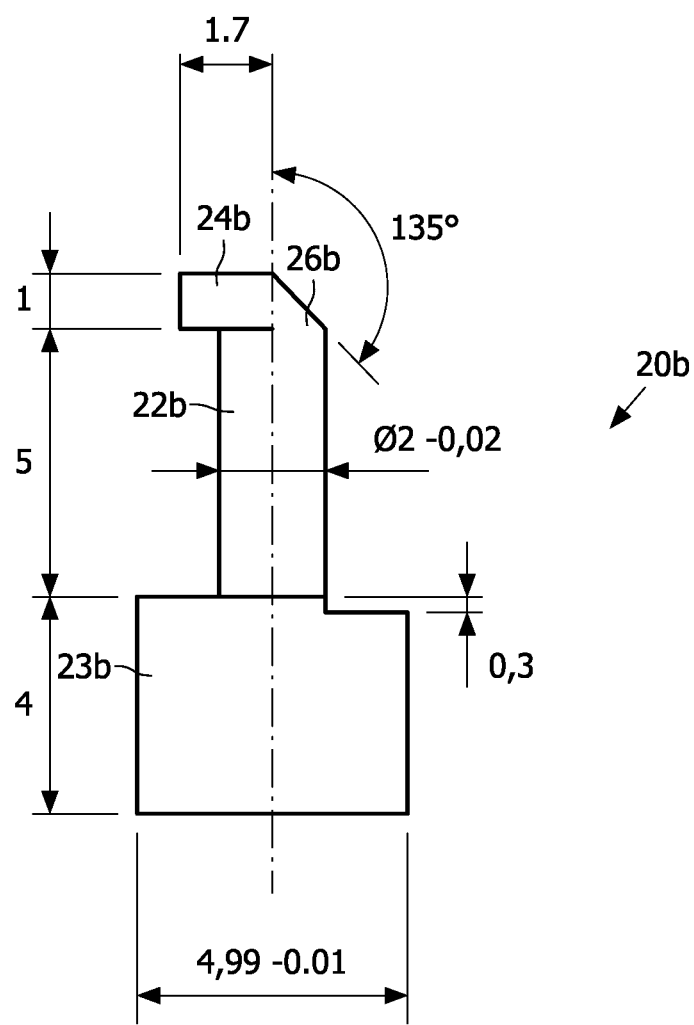
FIG. 2 shows a mechanical drawing of a side view of one magnetic subunit for use in the invention with indication of exemplary sizes in mm, FIG. 3 schematically shows a side view of an example of the two magnetic subunits arranged below the cartridge with another magnetic coil arranged above the cartridge and the alignment of magnetic field lines along the cartridge, with schematic magnetic particles near the sensor surface not true to scale for illustration, FIG. 4 schematically shows a side view of a biosensor system with the other magnetic coil, the top coil, above the cartridge, a cartridge and two subunits below the cartridge having slim shaped tips at each one end of the magnetic subunits, FIG. 5 schematically shows a side view of a biosensor system similar to FIG. 4 with the other magnetic coil, the top coil, above the cartridge, a cartridge and two subunits below the cartridge having bulky shaped tips at each one end of the magnetic subunits.

FIG. 2 shows a mechanical drawing of a particular magnetic subunit 20b for use in a magnet assembly 10, 40 similar to FIG. 1. Especially, the top surface 24b of the magnetic subunit 20b is depicted and further described. The same holds for a subunit 20a arranged opposite to the subunit 20b, as described. The dimensions of the subunit 20b as specified in FIG. 2 are denoted in millimeters (mm). In the shown particular embodiment, the base structure 23b has a height of 4 mm. In particular, the height of the base structure 23b of the subunit 20b may be between 2 to 10 mm, more preferably between 3 and 6 mm. The height of the core 22b is specified in FIG. 2 as being 5 mm. In a particular embodiment, the height of the core 22b may be between 3 and 10 mm, more preferably between 4 and 7 mm. The height of the tip 24b of the subunit 20b is specified as being around 1 mm. In a particular embodiment, the height of the tip 24b may be between 0.5 and 3 mm, more preferably between 0.5 and 2 mm. The length of the plane section of the top surface 24b of the core 22b is specified in FIG. 2 as being 1.7 mm. In a particular embodiment, the length of the plane section 28b may be between 1 and 3 mm, more preferably between 1.5 and 2 mm. The inclined section 26b of the tip or top surface 24b is specified in FIG. 2 as being 135°. In a particular embodiment, that angle may be between 100° to 170°, preferably between 120° to 150°, more preferably between 130 to 140°. The diameter of the cylindrical core 22b of the subunit 20b is specified in FIG. 2 as being between 0.02 and 2 mm. In a particular embodiment, the diameter of the core 22b is between 0.01 and 5 mm. Opposite side edges of the base structure 23b of the subunit 20b may be provided with an offset having a height of 0.3 mm according to the embodiment shown in FIG. 2. In a particular embodiment, the height of the offset may be between 0.1 and 0.5 mm, preferably between 0.2 and 0.4 mm. The length of the base structure 23b of a subunit 20b is specified in FIG. 2 as being between 0.01 and 4.99 mm. In a particular embodiment, the length and/or width of the base structure 23b ranges between 0.01 and 10 mm, preferably between 0.01 and 7 mm, or is, more preferably, less than 5 mm. These dimensions described hold for the magnetic subunit 20a accordingly.

In a particular embodiment, the length of the magnet assembly 10, 40 is essentially equal to the length of the biosensor cartridge 30. In this case, the magnetic field generated by the subunits 20a, 20b may penetrate the whole volume of the cartridge 30. In doing so, the particles 2 may be controlled in each section of the cartridge 30 to obtain reliable test results.

Figure 3:
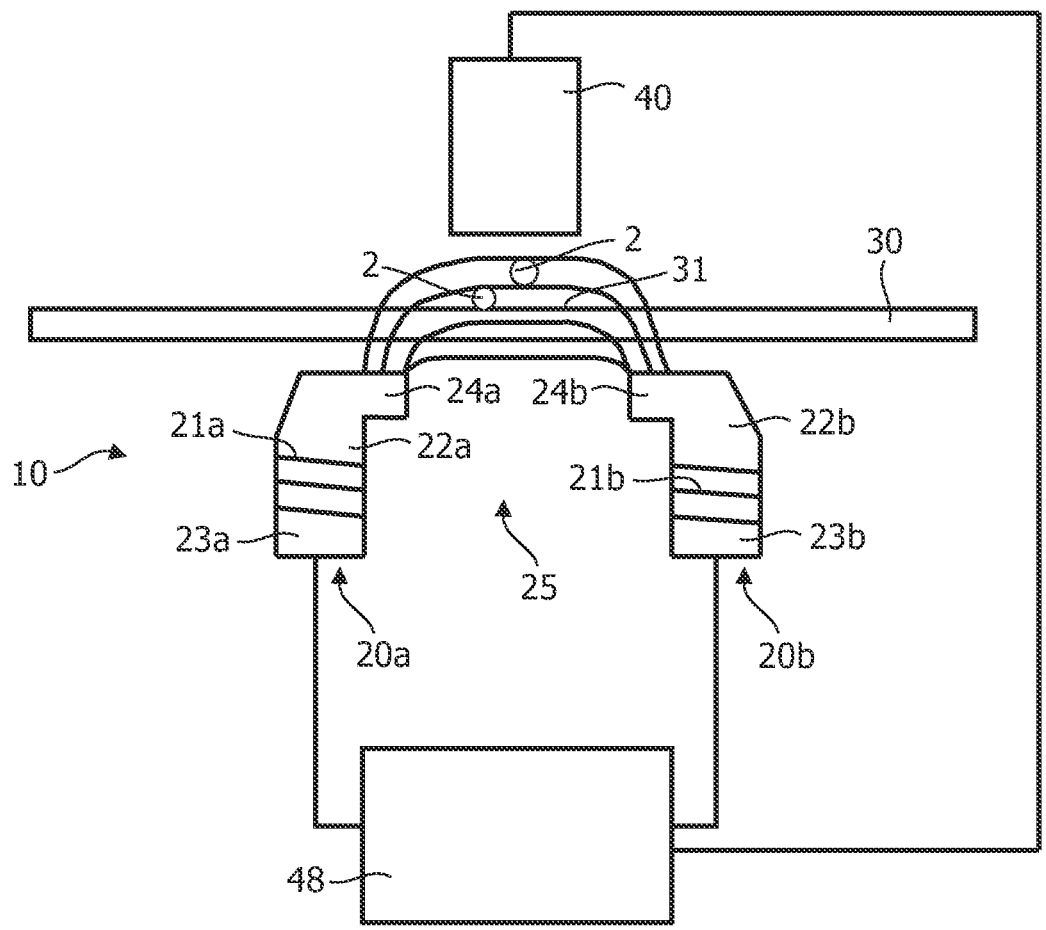

FIG. 3 shows a schematic side view of an example of the two magnetic subunits 20a, 20b arranged below the cartridge 30 similar to FIG. 1. When the sensor surface 31 in the cartridge 30 above the magnetic subunits 20a, 20b has a larger distance to the tips 24a, 24b, typically a wider gap 25 between the magnetic subunits 20a, 20b, is used. The subunits 20a, 20b are spaced from each other by the gap 25. The gap 25 is not necessarily filled with any material but with the ambient air to allow the subunits 20a, 20b being moved with respect to each other. In a further embodiment, the gap 25 may be filled with a dielectric material. The dielectric material may be a plastic moulding material, into which the subunits 20a, 20b may be embedded such that the outer shape of each subunit 20a, 20b is not apparent. In a preferred embodiment, only one or both of the pole surfaces of each subunit 20a, 20b is/are not covered by the dielectric material. The dielectric material may function as an insulator between the subunits and may fix the distance between the subunits 20a, 20b such that the subunits 20a, 20b are not moveable with respect to each other. Hence, geometrically constraints may further be avoided. Typically, the gap 25 between the magnetic subunits 20a, 20b is in the same order of magnitude as the distance of the magnetic subunits 20a, 20b to the sensor surface 31. The coils 21a, 21b are schematically indicated to further illustrate the described design and form of the magnetic subunits 20a, 20b. Various combinations of polarities of the two magnetic subunits 20a, 20b may be used (north-south, north-north, south-south, south-north). FIG. 3 sketches a configuration with opposing poles of the tips 24a, 24b. In this configuration the magnetic field lines between the poles of the two subunits 20a, 20b have a direction essentially parallel to the cartridge 30 in the area above the cartridge 30 and the sensor surface 31 at the cartridge 30. This effect is exemplary and schematically shown by four field lines originating from one pole of a magnetic subunit 20a and projecting to the second pole of the opposed subunit 20b. The shape of the magnetic field generated by the magnet assembly 10, 40 resembles an arc. As a result, the field lines penetrate the sample volume, in which sample the analyte is dissolved, e.g. salive or blood, under different angles, depending on the lateral position of the cartridge 30 with respect to the magnetic subunits 20a, 20b. Another important feature of the magnetic field in this configuration of the poles is that it has a magnetic field gradient that is directed towards the sensor surface 31, by which a force on the magnetic particles 2 towards the sensor surface 31 is exerted.

A further magnetic assembly, referred to as second magnet assembly 40 is arranged above the cartridge 30, as can be seen in FIG. 3, which is depicted in a schematic way. The second magnet assembly 40 is controllable separately by the biosensor system 1 and is for example designable as a coil or a magnet assembly 40 with multiple magnetic subunits. The second magnet assembly 40 can be designed similar to one or both of the magnetic subunits 20a, 20b. In the case of a second magnet with a single-core single-coil architecture, in the area between the second magnet assembly 40 and the cartridge 30 the magnetic field lines are nearly perpendicular to the cartridge 30 when only the second magnet assembly 40 is activated and the magnetic field generated by the two magnetic subunits 20a, 20b is deactivated. Magnetic forces originating from the second magnet assembly 40 affect the magnetic particles 2 and force the magnetic particles 2 away from the cartridge 30. Having controlled the second magnet assembly 40 and the two subunits 20a, 20b by the control means 48 in a coordinated way allows a controlled exertion of forces at the magnetic particles 2 in the fluid to be analyzed with regard to the plane of FIG. 3. For the sake of completeness the control means 48 is drawn in a schematic way which drives the two subunits 20a, 20b and the second magnet assembly 40. The control means 8 switches on and off and controls the magnetic field strength of the two subunits 20a, 20b and the second magnet assembly 40 according to the operating state. Operating states are for instance the parallel washing state, in which forces are exerted in an essentially parallel direction to the sensor surface 31 to wash away excessive beads 2. Another operating state is the actuation state in which beads 2 are dragged to the sensor surface 31 to establish a binding at an assay (not shown). The process of binding beads 2 with analytes and antigens to an assay (not shown) is known and described in the state of the art. With the biosensor system 1 described the binding process and the speed of this process is improved, as beads 2 approach the assay (not shown) faster due to magnetic forces. The distance between the tips 24a, 24b, of the two subunits 20a, 20b is chosen with respect to the distance to the location where the magnetic beads 2 are to be actuated, which is the area above the sensor surface 31 in the cartridge 30. The term actuation is known in the art and essentially means the process of providing magnetic particles 2 to an assay (not shown) to bind magnetic particles 2 and the analyte to the assay (not shown) with different methods known in the art. Furthermore, the biosensor system 1 described can also be applied to a biosensor cartridge 30 in which a measurement is done without binding the analyte and the magnetic particles 2 to an assay (not shown).

Figure 4:
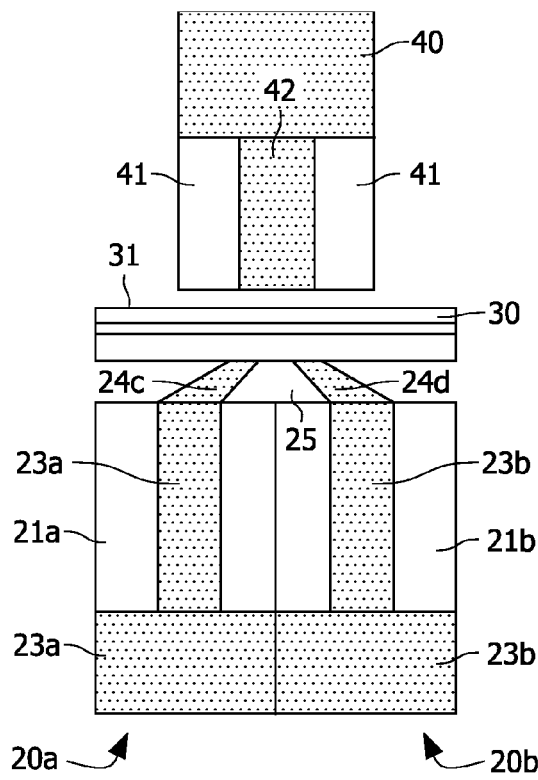
Figure 5:
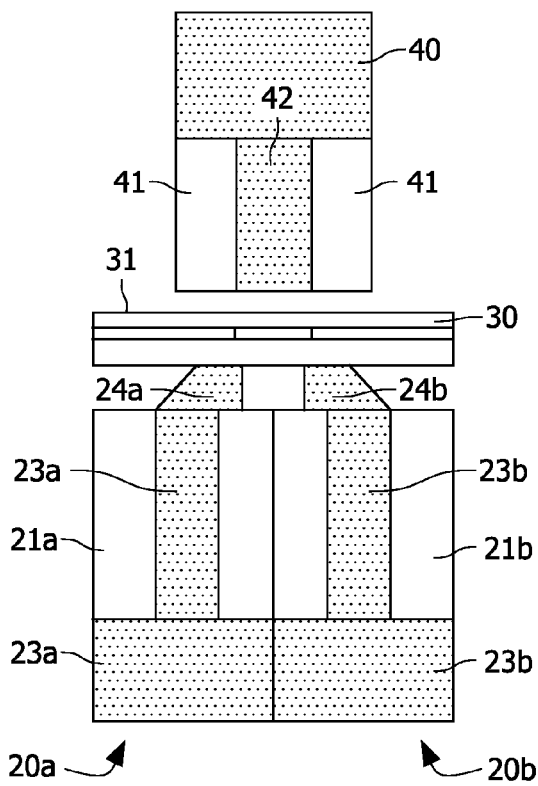

FIG. 4 schematically shows a side view of a bio sensor system 1 similar to FIG. 1 showing a certain example of top surfaces 24c, 24d, another example of top surfaces 24a, 24b is shown in FIG. 5. As in FIG. 3, the biosensor system 1 additionally comprises a second magnet assembly 40 on top of the biosensor system 1 comprising a core 42 and a coil 41, the second magnet assembly 40 is arranged above the cartridge 30 with reference to the illustration of the Figs. The second magnet assembly 40 is arranged at the other side of the cartridge 30 of the subunits 20a, 20b, the cartridge 30 including the sensor surface 31 is positioned between the second magnet assembly 40 and the two subunits 20a, 20b. The two subunits 20a, 20b under the cartridge 30 are separated by the gap 25 in the area of the tips 24c, 24d of the magnetic subunits 20a, 20b. This means a recessed area is arranged between the tips 24c, 24d which are regularly formed integrally with each subunit 20a, 20b, as indicated in FIG. 4, FIG. 5. As described the top surfaces or tips 24a, 24b, 24c, 24d are aligned in the direction to the sensor surface 31. In the example of FIG. 4 the tips 24c, 24d have a shape which is described as slim, which means the diameter of these examplary tips 24c, 24d lowers in the direction away from the cores 23a, 23b. With other words the tips 24c, 24d taper in the direction to the cartridge 30. The tips 24c, 24d in this example are slanted in the direction to each other, as visible in FIG. 4, leading to a narrower gap 25 near to the cartridge 30 than far from the cartridge 30 and near to the base structure 23a, 23b of the subunits 20a, 20b. In the example of FIG. 5 the tips 24a, 24b have a shape which is described as bulky, which means the diameter of these examplary tips 24a, 24b is essentially constant in the direction away from the subunits 20a, 20b. The tips 24a, 24b in FIG. 5 are shaped similar to the tips 24a, 24b described in detail under FIG. 2. The tips 24a, 24b extend in a direction essentially perpendicular to the cores 23a, 23b as depicted in FIG. 5, with the end faces of the tips 24a, 24b far from the cores 23a, 23b being opposed. This means the width of the gap 25 between the tips 24a, 24b is constant contrary to FIG. 4. Both examples described under FIG. 4, FIG. 5 result in a magnetic field characterized by field lines depicted in the similar example of FIG. 3. The consequences of the different examples of tips 24a, 24b, 24c, 24d for the profile of the magnetic field generated are described on basis of the curve under FIG. 6.

Figure 6:
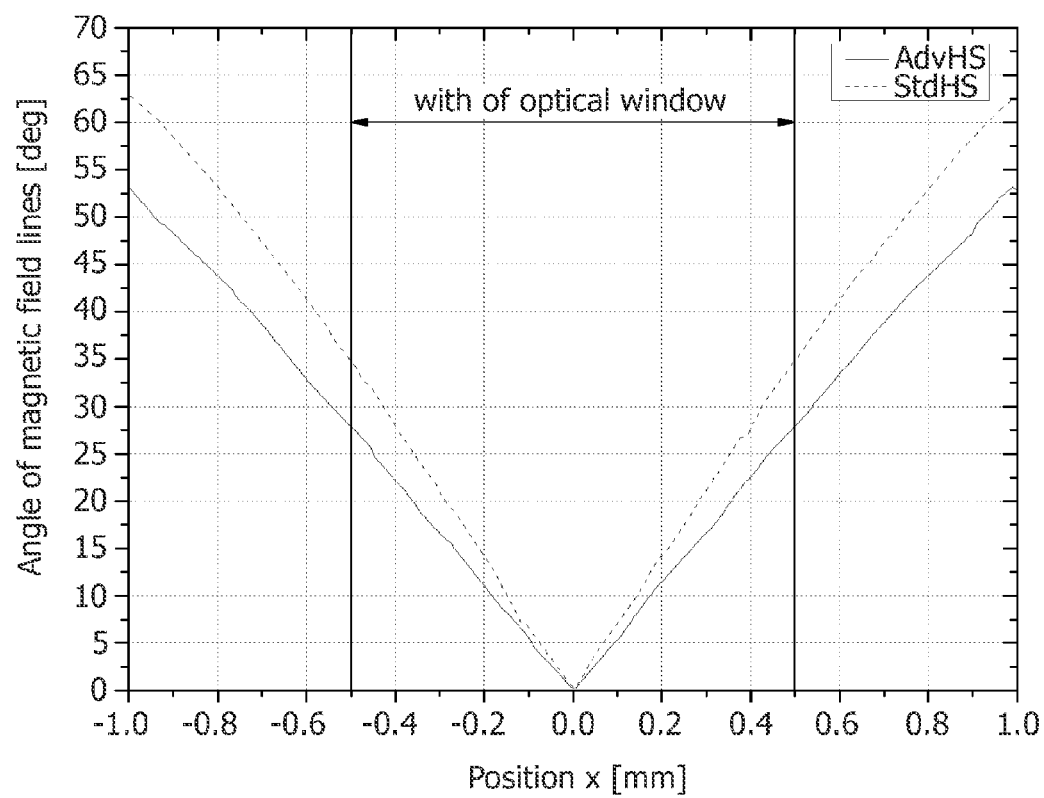
FIG. 6 shows two curves of the angle of magnetic field lines against the position at the sensor surface for the slim shaped tips according to FIG. 4 with a dashed line and for the bulky shaped tips according to FIG. 5 with a continuous line.

FIG. 6 shows two curves obtained in connection with the biosensor system 1, the x-axis denotes the position x along the sensor surface 31 of the cartridge 30 in mm. The y-axis denotes the angle α of the magnetic field lines. The angle α between the field lines and the optical window can be calculated from tanα=

$$\tan\alpha = \frac{B_y}{B_x},$$

with
$B_x$ and $B_y$ being the lateral and vertical components of the magnetic flux density vector, respectively. FIG. 6 shows the dependence of the angle α on the lateral position on the bottom of the sample volume. The edges of the optical window 46 are depicted in FIG. 6 by the perpendicular lines at the positions −0.5 mm and +5 mm. It can be seen that the field lines at the edge of the optical window 46 are slanted by about 30°. Due to the symmetry of the magnetic field at equal current input into both coils 21a, 21b, the field lines are running horizontally in the center of the optical window 46 at position zero. The upper dashed curve characterizes the angle α for the shape of slim tips 24c, 24d according to FIG. 4. The lower continuous curve characterizes the angle α for the shape of bulky tips 24a, 24b according to FIG. 5. The angle α enclosed by the magnetic field lines and the surface of the optical window 46 depends on the lateral position x on a horizontal line along the sensor surface 31. As shown by the curves the angle α has a value of zero at position zero, i.e. in the center of the optical window 46 field lines are parallel to the sensor surface 31. The angle α increases nearly continuously with increasing distance from the center at position zero. The upper dashed curve runs steeper than the lower continuous curve, which means the angle α has a stronger increase with the slim tips 24c, 24d according to FIG. 4 compared to the bulky tips 24a, 24b according to FIG. 5. The change in the geometry leads to a reduction of the field angle α of about 7° at the edge of the optical window 46. The shape of the tips 24a, 24b, 24c, 24d influences the angle α of magnetic field lines and therefore the exertion of forces at magnetic particles 2, as is proved by FIG. 6. As a result of the poletips or tips 24a, 24b, 24c, 24d geometry, the magnetic field distributions for the examples of magnetic subunits 20a, 20b according to FIG. 4 and FIG. 5 differ.

In experiments it has been observed that on basis of the magnetic subunit 20a, 20b according to FIG. 4 with slim tips 24c, 24d beads or magnetic particles 2 form chains during magnetic attraction, which ultimately attach to the sensor surface 31 or surface in the cartridge 30, and the chains align themselves according to the local orientation of the magnetic field lines. This effect has been identified as one cause of non-uniform distributions of magnetic particles 2 on the sensor surface 31, which is unwanted as the effect can impair correct measurements.

The biosensor system 1 comprising the altered geometry of bulky tips 24a, 24b featuring a flattened distribution of angles α has a wider arc of magnetic field lines avoiding the formation of chains of magnetic particles 2 and thus improving the distribution of the magnetic particles 2.

Figure 7:
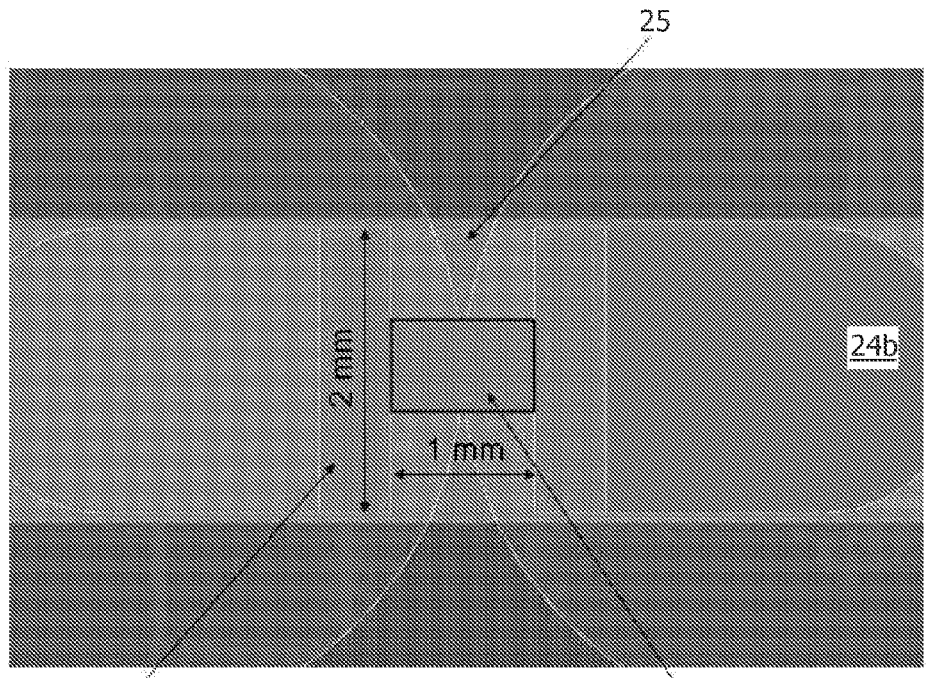
FIG. 7 shows a schematic top view of two narrow tips of magnetic subunits, a distribution of the magnetic field in the gap between the tips and an optical window between the tips in which area a measurement is done.

FIG. 7 shows a schematic top view of two tips 24a, 24b of the magnetic subunits 20a, 20b opposed to each other. In this example the distance between the tips 24a, 24b is chosen to about 1 mm. The width of the tips 24a, 24b is chosen to about 2 mm, which width is hereby referenced as narrow. Both dimensions, the width of the tips 24a, 24b and the distance between the tips 24a, 24b, can be chosen different. In the gap 25 and around the tips 24a, 24b a distribution of the magnetic field is shown, whereas in the center of the gap 25 the magnetic field lines are essentially parallel with regard to the end faces of the tips 24a, 24b. In the direction to the edges of the tips 24a, 24b, in FIG. 7 along a vertical line, far from the center of the gap 25 the magnetic field lines bend more and more in the direction around the tips 24a, 24b, capturing an increasing angle with the parallel magnetic field lines in the center of the gap 25. In FIG. 7 between the tips 24a, 24b an area is plotted centered in the gap 25 which area is the optical window 46. As described above one method to detect the analyte present in the cartridge 30, typically after the process of actuation, is an optical detection method. Other detection methods are designable. In the area of the optical window 46 the magnetic field is aligned in a way described with essentially parallel magnetic field lines. A measurement of the biosensor system 1 is done preferably in the optical window 46, consequently the sensor surface 31 and the analyte is placed in the optical window 46 above the tips 42a, 42b, as is shown in FIG. 3, FIG. 4, FIG. 5.

Figure 8:
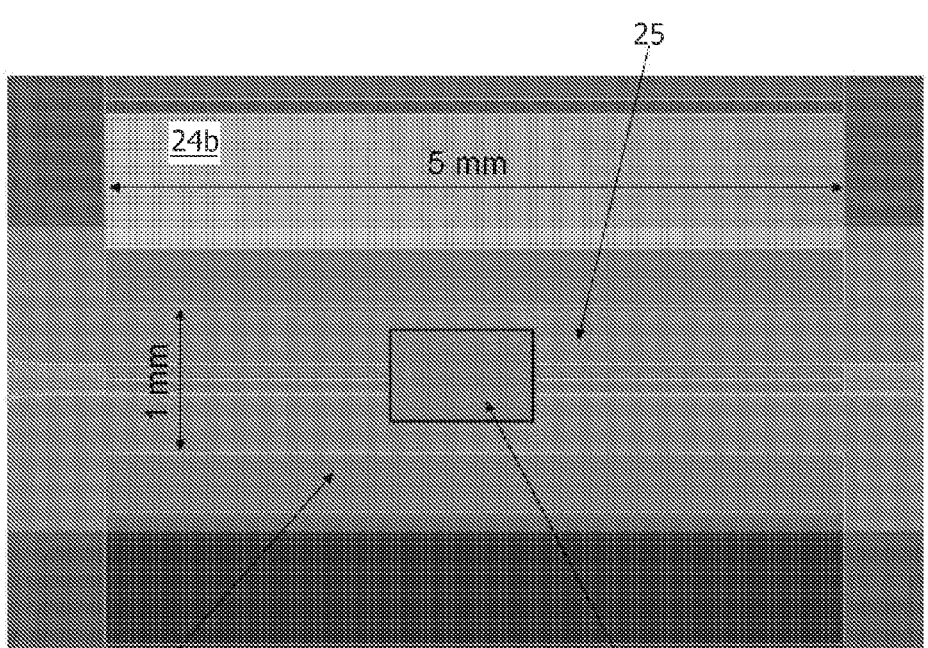
FIG. 8 shows a schematic top view similar to FIG. 7 of two broad tips of magnetic subunits, a distribution of the magnetic field in the broad gap between the tips and an optical window between the tips in which area a measurement is done.

FIG. 8 shows a schematic top view similar to FIG. 7 of two tips 24a, 24b of magnetic subunits 20a, 20b. The view onto the configuration shown in FIG. 8 is turned by 90° in comparison to FIG. 7. The tips 24a, 24b of the magnetic subunits 20a, 20b in FIG. 8 have a width of about 5 mm and therefore are broader than the tips 42a, 42b in FIG. 7. The distance between the tips 24a, 24b in the gap 25 in the example of FIG. 7 is roughly the same as the corresponding distance in FIG. 8 and chosen as 1 mm. The distribution of the magnetic field lines in the broad gap 25 of FIG. 8 between the tips 24a, 24b is different to the narrow gap 25 of FIG. 7, as depicted. The magnetic field lines are essentially parallel along a broad area within the broad gap 25, which area has at least the length of the width of the tips 24a, 24b, which is about 5 mm in the example given. An optical window 46 between the tips 24a, 24b in the gap 25 is shown in which area a preferred measurement of the biosensor system 1 is done. In FIG. 8 the optical window 46 is shiftable along a horizontal line without imparing the results of the measurement. This means the sensor surface 31 of the cartridge 30 can also be positioned in the direction to the edges of the tips 24a, 24b rather than only in the center of the gap 25. This is by reason of the magnetic field in the gap 25 being more homogeneous in comparison to FIG. 7 due to the structural changes of the tips 24a, 24b.

While the invention has been illustrated and described in detail in the drawings and foregoing description, such illustration and description are to be considered illustrative or exemplary and non-restrictive; the invention is thus not limited to the disclosed embodiments. Variations to the disclosed embodiments can be understood and effected by those skilled in the art and practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims and the description (for example, the functions of the control means as discussed above). The mere fact that certain measures are recited in mutually different dependent claims does not indicate that a combination of these measures can not be used to advantage. Any reference signs in the claims should not be considered as limiting the scope.

The invention claimed is:
1. A biosensor system, comprising:
a biosensor cartridge;
a first biosensor magnet assembly for generating a first magnetic field in the biosensor cartridge comprising two magnetic subunits each having a core with a top surface separated by a gap, the core tapering in the direction of the biosensor cartridge and having an incline section inclined by 120° to 150° with reference to the perpendicular of the sensor surface of the biosensor cartridge; and wherein a sensor surface comprised by the biosensor cartridge is arranged above the top surfaces of the cores, wherein the two subunits are adapted to generate the first magnetic field between the first subunit and the second subunit with first magnetic field lines essentially in parallel to the sensor surface to exert forces at magnetic particles in the cartridge;

wherein a second biosensor magnet assembly is arranged above the sensor surface for generating a second magnetic field and exerting a force on magnetic particles in the cartridge;

control means for separately controlling the second magnetic field by electrically driving at least one of the second biosensor magnet assembly and the two magnetic subunits;

wherein the control means causes the second magnetic field to include second magnetic field lines directed nearly perpendicular to the sensor surface, the second magnetic field lines acting as magnetic walls which block the magnetic particles from translating in a direction nearly in parallel to the sensor surface.

2. The biosensor system of claim 1, where the magnetic subunits and the second magnet assembly are arranged such that magnetic forces can be generated towards the sensor surface and away from the sensor surface by electrical control of the control unit.

3. The biosensor system of claim 2, wherein the whole analysis volume of the biosensor cartridge is affectable by the magnetic field generated by the subunits.

4. The biosensor system of claim 1, wherein each of the top surfaces has a plane section spaced between 0.1 mm to 5 mm from the sensor surface.

5. The biosensor system according to claim 1, wherein the control means controls the diffusion of magnetic particles in the cartridge by accelerating or decelerating movement of the magnetic particles in each spatial direction.

6. The biosensor system according to claim 1, wherein the biosensor cartridge includes a first region and a second region separated by the magnetic walls.

7. The biosensor system according to claim 6, wherein the magnetic particles present in the second region are hindered from moving into the first region by the magnetic walls.

8. A method for actuating magnetic particles with a biosensor system, comprising:
generating a first magnetic field in a biosensor cartridge with a first biosensor magnet assembly, wherein the biosensor cartridge comprises (i) two magnetic subunits each having a core with a top surface separated by a gap, and (ii) a sensor surface arranged above the top surfaces, and the first magnetic field is generated between the first subunit and the second subunit with magnetic field lines essentially in parallel to the sensor surface to exert forces at magnetic particles in the cartridge;
generating magnetic walls within the cartridge with the first biosensor magnet assembly, the magnetic walls preventing the magnetic particles from undergoing translational motion while still allowing for vertical motion;
generating a second magnetic field with a second biosensor magnet assembly arranged above the sensor surface, the second magnetic field exerting a force on the magnetic particles in the cartridge; and
coordinately controlling the first and second magnetic fields (i) in a parallel washing state, which push the magnetic particles away from the sensor surface, and (ii) an in actuation state, which drag the magnetic particles towards the sensor surface
wherein at least one of the first and the second biosensor magnet assembly generate a pre-determined magnetic field gradient in a direction at least one of parallel and perpendicular to the sensor surface in the biosensor cartridge.

9. The method of claim 8, wherein the magnetic field gradient steers the movement of magnetic particles present in a first region of the biosensor cartridge, and wherein magnetic particles present in a second region of the biosensor cartridge are hindered to move into the first region by the magnetic walls.

10. The method of claim 8, comprising a step of changing the polarity of at least one of the magnetic subunits.

11. The method of claim 8, wherein the two subunits are adapted to generate magnetic field lines directed from the first subunit to the second subunit and from the second subunit to the first subunit subsequently to wash away unbound magnetic particles.

12. A biosensor system, comprising:
a biosensor cartridge including a sensor surface;
a first biosensor magnet assembly for generating a first magnetic field in the biosensor cartridge comprising two magnetic subunits each having a core with a top surface arranged below the sensor surface, the two subunits structured to generate a magnetic field between the first subunit and the second subunit with magnetic field lines essentially in parallel to the sensor surface to exert forces at magnetic particles in the cartridge;
a second biosensor magnet assembly disposed above the sensor surface for generating a second magnetic field in the biosensor cartridge; and
a control unit for separately electrically controlling the two magnetic subunits and the second bio sensor magnet assembly to generate forces which attract the magnetic particles towards the sensor surface and pull the magnetic particles away from the sensor surface, the control unit configured to:
vary at least one of the first and second magnetic fields to have a magnetic gradient in a direction either parallel or perpendicular to the sensor surface of the biosensor cartridge; and
generate magnetic walls in the magnetic gradient which block the magnetic particles from translating in a direction nearly in parallel to the sensor surface.

13. The biosensor system according to claim 12, wherein the control unit is adapted to separately switch or adjust the magnetic field strength of each magnetic subunit or the second biosensor magnet assembly by electrical control.

14. The biosensor system according to claim 12, wherein the core with the top surface has an inclined by 120° to 150°, with reference to the perpendicular of the sensor surface of the biosensor cartridge.

15. The biosensor system according to claim 12, wherein the control unit is a single processor configured for driving the two magnetic subunits and the second magnet assembly.

16. The biosensor system according to claim 12, wherein the top surfaces of each core are separated by a gap distance which is narrower near the biosensor cartridge and wider away from the biosensor cartridge.

17. The biosensor system according to claim 12, wherein the top surface of each core includes an end face and the end faces are opposed.

18. The biosensor system according to claim 17, wherein the end faces are separated by a distance of about 1 mm.

* * * * *